United States Patent [19]

Ward et al.

[11] Patent Number: 5,208,360

[45] Date of Patent: May 4, 1993

[54] GLYCEROXYFUNCTIONAL SILANES AND SILOXANES

[75] Inventors: Andrew H. Ward, Sanford; Stefan F. Rentsch, Midland, both of Mich.; Alfred J. DiSapio, Greenwich, Conn.

[73] Assignee: Dow Corning Corporation, Midland, Mich.

[21] Appl. No.: 832,191

[22] Filed: Feb. 6, 1992

Related U.S. Application Data

[62] Division of Ser. No. 681,584, Apr. 8, 1991, Pat. No. 5,145,875, which is a division of Ser. No. 489,117, Mar. 5, 1990, Pat. No. 5,043,359.

[51] Int. Cl.$^5$ .............................. C07F 7/04; C07F 7/08
[52] U.S. Cl. ..................... 556/444; 556/449; 556/482
[58] Field of Search ................. 514/63, 772; 556/449, 556/444, 482

[56] References Cited

U.S. PATENT DOCUMENTS

| | | | |
|---|---|---|---|
| 4,013,698 | 3/1977 | Lohse et al. | 556/449 X |
| 4,254,104 | 3/1981 | Suzuki | 424/170 |
| 4,431,632 | 2/1984 | Burns | 424/81 |

*Primary Examiner*—Leonard Schenkman
*Attorney, Agent, or Firm*—Jim L. DeCesare

[57] ABSTRACT

Compositions and a method of delivering a humectant to a surface such as skin by forming a reaction product of the humectant with an organosilicon compound. The reaction product is applied to the skin surface and contacted with moisture which causes the reaction product to undergo hydrolysis on the skin surface. This releases free humectant onto the skin surface and the silanol functional organosilicon compound formed as a result of the hydrolysis can be utilized on the skin surface as a durable water repellent and softening ingredient for the skin.

3 Claims, No Drawings

GLYCEROXYFUNCTIONAL SILANES AND SILOXANES

RELATED PATENT APPLICATIONS

This application is a division of U.S. application Ser. No. 07/681584 filed Apr. 8, 1991, now U.S. Pat. No. 5,145,875 issued Sep. 8, 1992, which is in turn a division of U.S. application Ser. No. 07/489117 filed Mar. 5, 1990, now U.S. Pat. No. 5,043,359 issued Aug. 27, 1991.

BACKGROUND OF THE INVENTION

This invention relates to the enhancement of the humectancy of skin conditioning compositions with certain organosilicon compounds. More particularly, certain glyceroxyfunctional organosilicon compounds are included as an ingredient in a skin conditioner.

Mineral oil is a highly refined, colorless, tasteless, and odorless, liquid mixture of hydrocarbons obtained from petroleum, that has been used medicinally as an internal lubricant and in the manufacture of various salves and ointments. It is also known as medicinal oil, white mineral oil, heavy mineral oil, light mineral oil, liquid paraffin, and paraffin oil. Mineral oil has long been the emollient of choice in creams and lotions. It is second only to water as a moisturizer ingredient. Mineral oil acts as a moisturizer primarily through the functioning of the ingredient as an occlusive barrier. The water content of the outer layers of the stratum corneum of the human skin is a controlling factor in the appearance of dry skin symptoms. When the stratum corneum contains an adequate amount of water within the range of ten to twenty percent, the skin remains flexible. However, when the water content falls below ten percent, the stratum corneum often becomes brittle and rough, and can exhibit scaling and cracking.

The stratum corneum receives its water from the deep layers of the epidermis by diffusion or when it is brought into direct contact with water. The diffusion process is controlled by the water content of the skin, as well as the concentration gradient. In a very dry environment, the water loss from the external skin layers can be significant and often exceeds the rate of replacement by diffusion. An occlusive barrier of mineral oil, for example, placed onto the surface of the skin acts to retard the water loss to the environment and allows the skin surface to rehydrate by the diffusion process. Due to the effectiveness, low cost, and safety, of petroleum derivatives such as mineral oil, it serves as a useful occlusive moisturizer and contributes to dry skin prevention by protection and moisture retention, as well as dry skin repair by emolliency, lubricity, and moisture restoration.

While mineral oil has been found to be an effective and economical emollient for skin care applications, and provides softening, smoothing, and a protective action on skin, it nevertheless suffers from the disadvantage that it is easily removed from the skin by washing the skin with soap. Thus, the effectiveness and long term benefits of mineral oil enumerated above are of a limited duration.

Accordingly, it is not uncommon to include in skin conditioning compositions a humectant which is capable of introducing moisture to the skin from the atmosphere in conditions of moderate or high humidity. In conditions of low humidity, humectants attract moisture from the lower layers of the skin. Humectants are materials which are hygroscopic therefore and capable of retaining moisture. Among the most well known water retentive humectant capable of preventing drying out is glycerol. Glycerol is known to be an effective humectant and is generally considered harmless in cosmetic applications. It is a clear, water-white viscous liquid having the chemical formula $HOCH_2CHOHCH_2OH$. Glycerol exhibits no bonding to the skin and hence is not substantive and can be washed from the skin surface. It is used in many creams and lotions for the purpose of keeping the skin soft and replacing skin moisture. Technically, the term glycerol connotes the pure compound 1,2,3-propanetriol whereas the term glycerin implies a product containing in excess of about ninety-five percent glycerol.

In accordance with the present invention, a novel delivery mechanism for glycerol has been discovered in which a reaction product is formed resulting in a glyceroxyfunctional organosilicon compound. Upon application to the skin, the reaction product hydrolyzes to release free glycerol. Organosilicon compounds which include the glyceroxy radical are not new. For example, in U.S. Pat. No. 3,741,917, issued Jun. 26, 1973; U.S. Pat. No. 3,933,407, issued Jan. 20, 1976; and U.S. Pat. No. 4,122,029, issued Oct. 24, 1978; there are described certain dimethylsiloxane copolymers which contain an intervening oxyalkylene group between the silicon atom on the main siloxane chain and the glyceroxy radical. In contrast, the compositions of the present invention include a glyceroxy radical directly bonded to the silicon atom on the main chain to form either silanes substituted with glyceroxy groups or dimethylsiloxane polymers substituted with glyceroxy groups.

SUMMARY OF THE INVENTION

This invention relates to compositions and to a method of delivering a humectant to a surface such as skin by forming a reaction product of the humectant with an organosilicon compound. The humectant-organosilicon reaction product is applied to the skin surface and contacted with moisture which causes the humectant-organosilicon reaction product to undergo hydrolysis on the skin surface. The hydrolysis forms free humectant and a silanol functional organosilicon compound as a result of the hydrolysis. This releases free humectant onto the skin surface and the silanol functional organosilicon compound can be utilized on the skin surface as a durable water repellent and softening ingredient for the skin.

These and other features, objects, and advantages, of the herein defined present invention will become more apparent from a consideration of the following detailed description thereof.

DETAILED DESCRIPTION OF THE INVENTION

In accordance with the present invention, there is provided both compositions and a method of delivering a humectant to a surface such as skin. A reaction product is formed which includes the humectant and an organosilicon compound selected from the group consisting of silanes and siloxanes. The humectant-organosilicon reaction product is then applied to the skin surface where the humectant-organosilicon reaction product on the skin surface comes into contact with moisture. The source of the moisture on the skin may be moisture in the air, moisture on the skin itself, or moisture as a result of perspiration. Contact with moisture causes the humectant-organosilicon reaction product to undergo hydrolysis on the skin surface with the result that there is formed free humectant along with a silanol functional organosilicon compound as a result of the hydrolysis. This functions to release free humectant onto the skin surface where the humectant performs its humectancy function. Simultaneously, the silanol functional organosilicon compound which is also formed as a result of the hydrolysis is utilized on the skin surface as a combination durable water repellent and softening ingredient for the skin.

Thus, the compositions of the present invention possess a dual role when incorporated into skin conditioning formulations, and the compositions contribute to the formulation various desirable attributes such as humectancy, water repellency, and softening.

Preferably, the humectant-organosilicon reaction product is applied to the skin surface in an anhydrous delivery vehicle. For example, the anhydrous delivery vehicle can be in the form of an ointment, dispersion, solution, lotion, cream, gel, or stick product. In the most preferred embodiment of the present invention, the humectant is glycerol, and the organosilicon compound is an alkylalkoxysilane such as methyltrimethoxysilane.

More particularly, the compositions of the present invention comprise an organosilicon compound having the formula selected from the group consisting of

wherein R is an alkyl radical of one to six carbon atoms or phenyl; Q is the glyceroxy radical -OCH$_2$CH(OH)CH$_2$OH; x is an integer having a value form zero to three; y is an integer having a value of from zero to about one thousand; and z is an integer having a value of from one to about twenty.

The most preferred reaction product is a glyceroxyfunctional silane of the formula (CH$_3$)$_3$SiOCH$_2$CH(OH)CH$_2$OH which is formed by combining glycerol and methyltrimethoxysilane. It is particularly useful in skin conditioning compositions for topical application which contain as an ingredient thereof at least one organosilicon compound, and in which the skin conditioning composition is free of water. The organosilicon compound of the present invention may be present in the skin conditioning composition in an amount of about five percent by weight, and is particularly suited for use where the skin conditioning composition constitutes a moisturizing cream.

Upon application to the skin, the compounds of the present invention hydrolyze to form silanol groups and free glycerol. The silanol groups bond to the skin and provide the benefits of water repellency and softening. The free glycerol provides humectancy which absorbs water vapor. The hydrolysis takes place over time slowly releasing the glycerol. The mechanism can be visualized as follows:

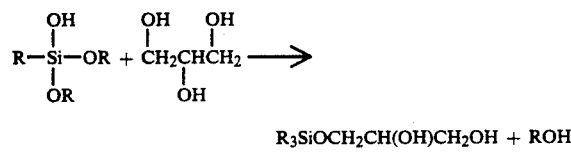

R$_3$SiOCH$_2$CH(OH)CH$_2$OH + ROH

R$_3$SiOH + HOCH$_2$CHOHCH$_2$OH

While the foregoing mechanism covers the concept of the present invention as it relates to silanes, a similar mechanism follows in the case of siloxanes. Thus:

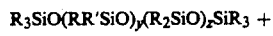

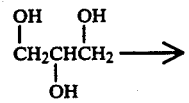

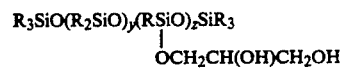

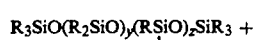

H$_2$O ⟶ HOCH$_2$CHOHCH$_2$OH +

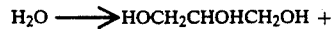

In the above siloxane mechanism, R' is preferably hydrogen, OH, or OR, in order to provide a reactive site. Where R' is hydrogen, hydrogen is a product of the reaction. Where R' is OH, water is also a product. Where R' is OR, the other product is ROH.

The compounds R$_3$SiOH and

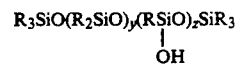

are both durable and substantive to the skin and provide the added benefit of forming a water repelling layer on the skin as well as contributing to the softening characteristics of the skin conditioning compositions into which they are included. This in combination with the free glycerol which acts as a humectant provides a novel and unique combination.

While the compounds of the present invention can be used for direct application to the skin, it is most preferred to include them as an ingredient in anhydrous topical skin conditioning compositions. For example, such anhydrous topical skin conditioning compositions suitable in accordance with the present invention can be of the type described in U.S. Pat. No. 4,335,104, issued Jun. 15, 1982, and in U.S. Pat. No. 4,355,046, issued Oct. 19, 1982; the disclosures of which are incorporated herein by reference. However, any anhydrous system is appropriate.

The compounds have been found to spread over skin in a fashion beyond that of glycerol itself which has a tendency not to wet the skin, and hence the compounds possess the added advantage of being film formers of improved spreadability. When mixed into conventional skin conditioning compositions, the compounds of the present invention extend the usefulness of glycerol over time, and as the glycerol is slowly released by hydrolysis with water, the preparations including the compounds are equivalent to prior art applications requiring multiple applications. The invention is further illustrated in the following examples.

EXAMPLE I

Into a flask was added 184 grams of glycerol. The glycerol was heated to about sixty degrees Centigrade for thirty minutes under a dry nitrogen purge. There was added to the flask 0.5 grams of sodium borohydride and 272 grams of MeSi(OMe)$_3$. Upon heating, a homogeneous clear mixture was obtained. The temperature was maintained at seventy-five degrees Centigrade for two hours. The flask was equipped with a Dean-Stark trap and 91 grams of 72% methanol/28% MeSi(OMe)$_3$ was removed, indicating the products MeSi(OMe)$_2$-(OCH$_2$CHOHCH$_2$OH) and MeSi(OMe)(OCH$_2$CHOHCH$_2$OH)$_2$.

EXAMPLE II

Example I was repeated employing a one to three molar ratio of MeSi(OMe)$_3$ and glycerol, and a viscous cloudy liquid was obtained similar to the product of Example I and containing MeSi(OMe)$_2$(OCH$_2$CHOHCH$_2$OH) and MeSi(OMe)(OCH$_2$CHOHCH$_2$OH)$_2$.

Examples of emollients and moisturizers which are compatible with this invention include straight, branched or cyclic hydroxy compounds such as alcohols containing 1 to 30 carbon atoms; straight, branched or cyclic carboxylic acids containing 1 to 31 carbon atoms; acid esters containing C$_1$ to C$_{30}$ carboxylic acids esterified with C$_1$ to C$_{30}$ alcohols; alcohol ethers containing 1 to 30 carbon atoms; alkanes of the formula H—(CH$_2$)n—H, wherein n is 5 to 30; and siloxanes. Examples of such functional materials include 2-ethylhexyl oxystearate; arachidyl propionate; 2-ethylhexyl adipate; isopropyl myristate; ethanol; stearyl alcohol; propylene glycol; propionic acid; stearic acid; polyoxypropylene cetyl alcohol; polyoxypropylene lanolin alcohol; Carbowax ® 300; petroleum jelly, mineral oil; aliphatic hydrocarbons such as mineral spirits; lanolin and lanolin derivatives such as acetylated lanolin and isopropyl lanolate; hexamethyldisiloxane; cyclic polydimethylsiloxane; linear polydimethylsiloxane; polyphenylmethylsiloxane; and polydiemthyl/trimethylsiloxane. Other phenyl, ethyl and vinyl substituted siloxanes may also be included in the formulated products of this invention.

It will be apparent from the foregoing that many other variations and modifications may be made in the compounds, compositions, structures, and methods, described herein, without departing substantially from the essential features and concepts of the present invention. Accordingly, it should be clearly understood that the forms of the invention described herein are exemplary only and are not intended as limitations on the scope of the present invention as defined in the appended claims.

That which is claimed is:

1. An organosilicon compound having a formula selected from the group consisting of

wherein R is an alkyl radical of one to six carbon atoms or phenyl; Q is the glyceroxy radical —OCH$_2$CH(OH)CH$_2$OH; x is an integer having a value form zero to three; y is an integer having a value of from zero to about one thousand; and z is an integer having a value of from one to about twenty.

2. A compound having the formula R$_x$Si(Q)$_{4-x}$ in which R is an alkyl radical of from one to six carbon atoms or phenyl; Q is the glyceroxy radical —OCH$_2$CH(OH)CH$_2$OH; and x is an integer having a value of from zero to three.

3. A compound having the formula R$_3$SiO(R$_2$SiO)$_y$(RQSiO)$_z$SiR$_3$ in which R is an alkyl radical of from one to six carbon atoms or phenyl; Q is the glyceroxy radical —OCH$_2$CH(OH)CH$_2$OH; x is an integer having a value of from zero to three; y is an integer having a value of from zero to about one thousand; and z is an integer having a value of from one to about twenty.

* * * * *